(12) United States Patent
Gekeler et al.

(10) Patent No.: US 9,446,040 B2
(45) Date of Patent: Sep. 20, 2016

(54) SUBSTITUTED IMIDAZOQUINOLINES

(71) Applicant: 4SC AG, Planegg-Martinsried (DE)

(72) Inventors: Volker Gekeler, Constance (DE); Thomas Maier, Stockach (DE); Astrid Zimmermann, Mühltal (DE); Hans-Peter Hofmann, Düsseldorf (DE); Sanjeev A. Kulkarni, Pune (IN); Anil P. Jagtap, Satara (IN); Ganesh S. Chaure, Dist-Ahmednagar (IN)

(73) Assignee: 4SC AG, Planegg-Martinsried (DE)

( * ) Notice: Subject to any disclaimer, the term of this patent is extended or adjusted under 35 U.S.C. 154(b) by 0 days.

(21) Appl. No.: 14/729,698

(22) Filed: Jun. 3, 2015

(65) Prior Publication Data

US 2015/0335636 A1    Nov. 26, 2015

Related U.S. Application Data

(62) Division of application No. 12/934,228, filed as application No. PCT/EP2009/053399 on Mar. 23, 2009, now Pat. No. 9,073,913.

(30) Foreign Application Priority Data

Mar. 24, 2008  (IN) .......................... 614/MUM/2008

(51) Int. Cl.
*A61K 31/44* (2006.01)
*A61K 31/4745* (2006.01)
*C07D 471/04* (2006.01)

(52) U.S. Cl.
CPC ......... *A61K 31/4745* (2013.01); *C07D 471/04* (2013.01)

(58) Field of Classification Search
USPC ....................................................... 514/293
See application file for complete search history.

(56) References Cited

U.S. PATENT DOCUMENTS

| 6,069,149 | A | 5/2000 | Nanba et al. |
|---|---|---|---|
| 6,376,669 | B1 | 4/2002 | Rice et al. |
| 6,451,810 | B1 | 9/2002 | Coleman et al. |
| 7,897,767 | B2 | 3/2011 | Kshirsagar et al. |
| 2003/0144283 | A1 | 7/2003 | Coleman et al. |
| 2003/0199538 | A1 | 10/2003 | Skwierczynski et al. |
| 2004/0176367 | A1 | 9/2004 | Griesgraber et al. |
| 2004/0229897 | A1 | 11/2004 | Crooks et al. |
| 2006/0051374 | A1 | 3/2006 | Miller et al. |
| 2007/0166384 | A1 | 7/2007 | Zarraga |
| 2007/0259881 | A1 | 11/2007 | Dellaria, Jr. et al. |
| 2008/0015184 | A1 | 1/2008 | Kshirsagar et al. |
| 2008/0193474 | A1 | 8/2008 | Griesgraber et al. |
| 2009/0105295 | A1 | 4/2009 | Kshirsagar et al. |
| 2010/0280001 | A1* | 11/2010 | Bonnert ............... C07D 471/04 514/210.21 |

FOREIGN PATENT DOCUMENTS

| JP | 11-222432 A | 8/1999 |
|---|---|---|
| WO | 0076505 A1 | 12/2000 |
| WO | 2005003064 A2 | 1/2005 |
| WO | 2005048933 A2 | 6/2005 |
| WO | 2005048945 A2 | 6/2005 |
| WO | 2005123079 A2 | 12/2005 |
| WO | 2006-009832 A1 | 1/2006 |
| WO | 2006028451 A1 | 3/2006 |
| WO | 2006116475 A2 | 11/2006 |
| WO | 2008135791 A1 | 11/2008 |

OTHER PUBLICATIONS

International Search Report, dated Sep. 21, 2009, issued in corresponding PCT/EP2009/053399.
Written Opinion, dated Sep. 21, 2009, issued in corresponding PCT/EP2009/053399.
Coleman et al. CAS: 134: 56665, 2000.
WO 2008/135791 A1, Corrected Version. , 2008.

* cited by examiner

*Primary Examiner* — Rei-Tsang Shiao
(74) *Attorney, Agent, or Firm* — Millen White Zelano and Branigan, PC; Csaba Henter; Anthony Zelano

(57) ABSTRACT

Imidazoquinolines of formula I that contain substituted amine or amide functionality at 1-position and that are effective as Toll like Receptor 7 activators are disclosed. These compounds are useful as anticancer agents.

20 Claims, 7 Drawing Sheets

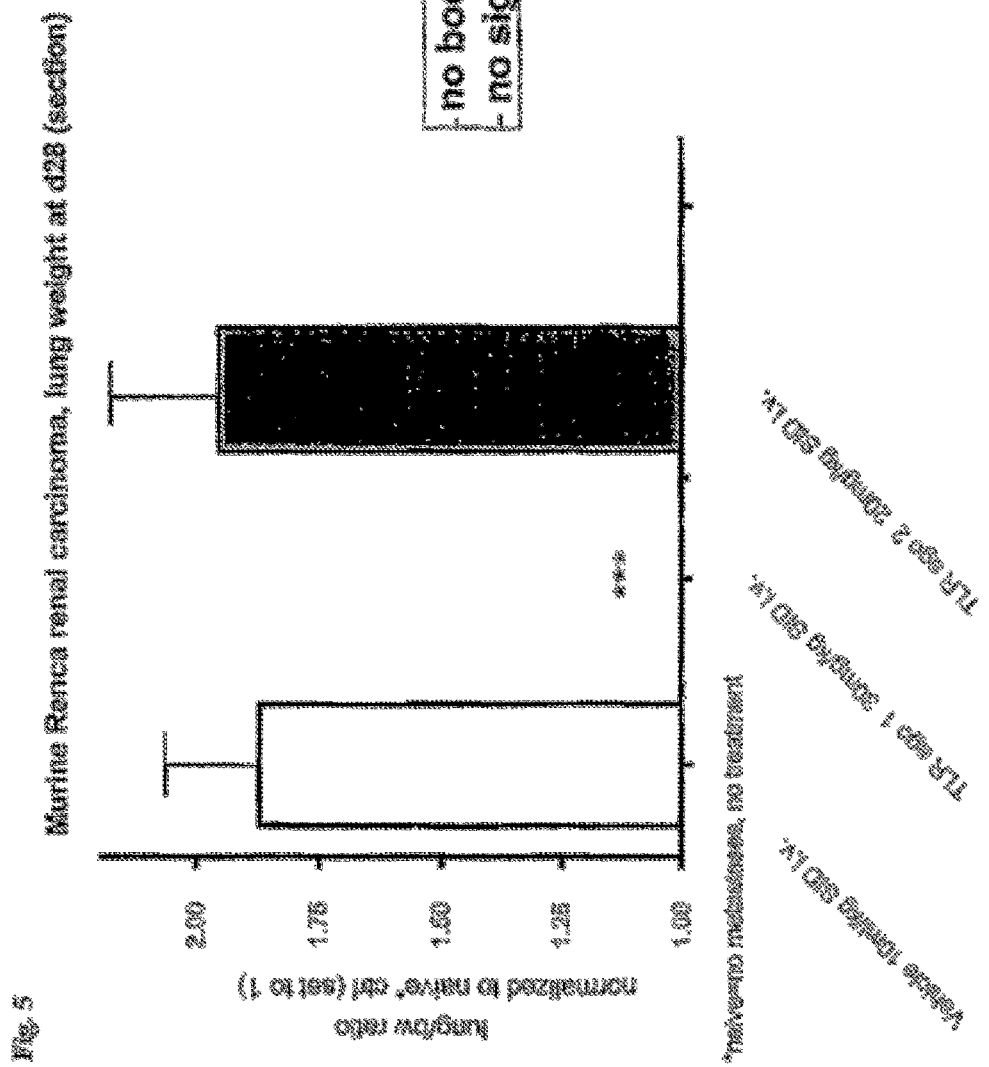

SUBSTITUTED IMIDAZOQUINOLINES

FIELD OF INVENTION

The invention relates to imidazoquinoline derivatives and to pharmaceutical compositions containing the imidazoquinoline derivatives. The imidazoquinoline derivatives are useful as toll-like receptor agonist/TLR7 activators.

BACKGROUND OF INVENTION

Toll-like receptors (TLR) currently comprising a gene family of 10 receptors with different specificities are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by E. coli lipopolysaccharide LPS), e.g. on epithelial cells, or TLR3, 7, 8 and 9 located at endosomal membranes in specified immune cells. The latter are all activated by nucleic acids, but recognize various types of them. For instance, TLR9 is activated by single stranded DNA containing CpG subsequences, TLR7 and 8 are activated by single stranded RNA, and TLR3 is activated by double-stranded RNA.

Some small-molecule (SMOL) TLR7 or TLR8 agonists have been identified. Those agonists can be grouped into purine-like molecules, such as 7-thia-8-oxoguanosine (TOG, isatoribine) or the imidazoquinoline imiquimod. Imiquimod is so far the only approved definitive TLR agonist, marketed as 5% créme (by Aldara). It generates approx 80% 5 year clearance of superficial basal cell carcinomas, which is the most frequent cancer worldwide. Imiquimod activates TLR7. The functional expression of TLR7 appears to be restricted to specified immune cells, i.e. in humans so far solely plasmacytoid dendritic cells, B-cells and probably eosinophils are known to be activated by TLR7 agonists.

For several years strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7 or TLR9 agonists are in clinical development for cancer mono- or combination therapies, or as vaccine adjuvant.

The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoform's altogether, and not only type I (alpha, beta), but also (indirectly) type II (gamma, NK cells). At least for local application, Aldara has delivered a remarkable proof-of-concept. This demonstrates that antigens are released by tumors, and that immune therapy can work for cancer indications in principle, and even in monotherapy. For a systemic administration route, though, the clinical POC is pending for TLR7 or TLR9 agonists, which both are in clinical trials. For advanced cancers and systemic application (preferably s.c. or i.v. administration route) it appears to be clear that such TLR agonists have to be combined with other therapies.

In case of earlier stages of cancer the situation might be different. Tumor metastasis is a most severe aspect of tumor development in patients, largely because tumors are detected too late when metastasis already has occurred. Established tumor therapies mostly include cytotoxic drugs with rather narrow therapeutic windows. Hence, for the treatment in earlier tumor stages, when the suppression of metastasis spread might still be possible, the need is high for new therapies with good tolerability and safety.

The activation of the immune system, and in particular, the activation of toll-like receptor (TLR) signaling offers new promising approaches. TLR9 agonistic CpG oligos like H2006 or H1826, and TLR7 agonists like the guanosine derivative isatoribine or an imiquimod derivative were tested in our murine Renca lung metastasis model. All tested molecules virtually completely suppressed the emergence of lung metastases with good tolerability. This provides a convincing rational for clinical development of such molecules for suppression of cancer metastasis and points to the possibility of systemic application of such drugs. However, the SMOL type TLR7 agonists have the advantage of established and cost effective synthesis if compared to the nucleic acid type TLR9 agonists, and are well suited for topical application.

U.S. Pat. No. 6,573,273 describes imidazoquinoline and tetrahydroimidazoquinoline compounds that contain urea, thiourea, acylurea, sulfonylurea or carbamate functionality. The compounds are said to be useful as immunomodulators.

U.S. Pat. No. 6,677,349 describes imidazoquinoline and tetrahydroimidazoquinoline compounds that contain sulfonamide functionality at the 1-position. The compounds are said to be useful as immunomodulators.

US-A-2003/0144283 and WO-A-00/76505 describe imidazoquinoline and tetrahydroimidazoquinoline compounds that contain amide functionality at the 1-position. The compounds are said to be useful as immunomodulators.

WO-A-2005/051324 describes imidazo-quinoline, pyridine and naphthyridine rind systems substituted in 1-position with oxime or a special N-oxide functionality. The compounds are said to be useful as immunomodulators.

SUMMARY OF INVENTION

Small molecules, in particular imidazoquinolines-4-amine derivatives, have been found that are activators for TLR7 with high potency. These imidazoquinoline derivatives have favorable physicochemical and pharmacokinetic properties. Accordingly, this invention provides compounds, which have been found to be activators for TLR7 and which are defined by general structure formula I:

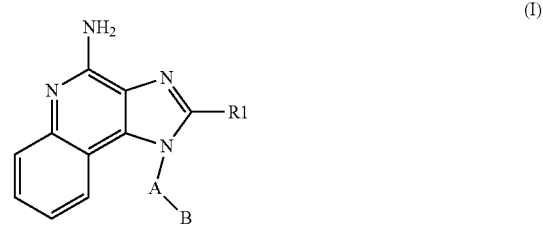

wherein: R1, A and B are as defined below.

The compounds of formula I are useful as TLR7 activators.

The invention further provides pharmaceutical compositions containing an effective amount of compound of formula I.

In addition, methods of synthesizing compounds of formula I are described.

BRIEF DESCRIPTION OF THE DRAWINGS

FIG. 5 shows studies similar to FIGS. 4A, 4B, 4C, 4D and 4E, however performed with 3-{acetyl[4-(4-amino-2-ethyl-1H-imidazo[4,5-c]quinolin-1-yl)butyl]amino}-2,5-anhydro-1,3,4-trideoxypentitol (TLR ago 1, example III) and N-[4-(4-amino-2-ethyl-1H-imidazo[4,5-c]quinolin-1-yl)butyl]-N-(1,1-dioxidotetrahydro-3-thienyl) acetamide (TLR ago 2, example I) in the Renca lung metastasis model.

DETAILED DESCRIPTION OF INVENTION

Figure 1:
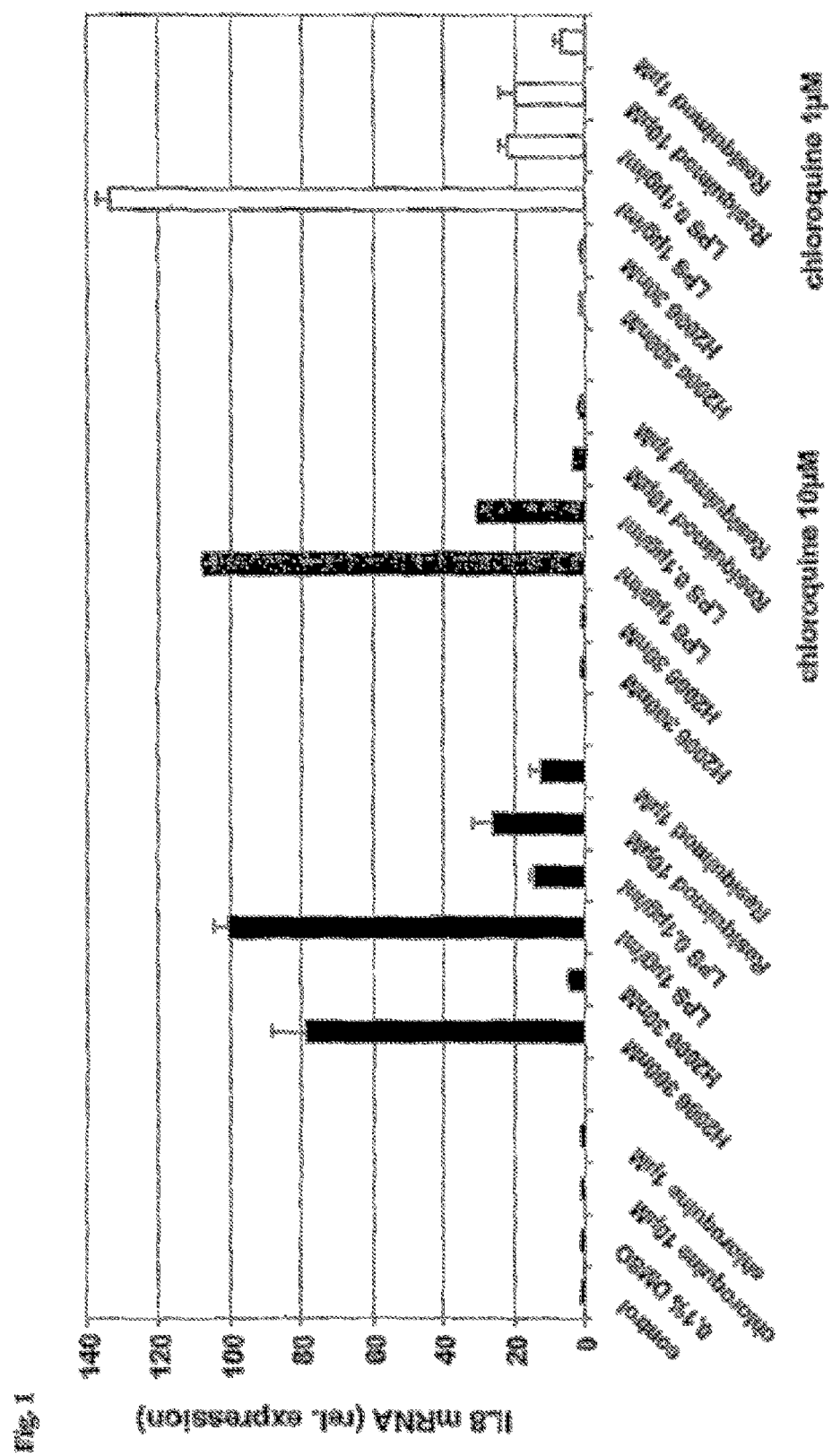
FIG. 1 shows the effect of chloroquine on cytokine induction of TLR agonists in PCIR-1 cells. Expression of IL8 mRNA was measured with TaqMan PCR after 16 hours incubation of cells with H2006, LPS or Resiquimod alone and in combination with cloroquine.

It has been found that the imidazoquinoles derivatives, which are described in greater details below, are effective TLR7 activators and have surprising and particularly advantageous properties.

In addition and based on the foregoing, it has also been found, that certain pharmaceutically acceptable solvates, salts, N-oxides or stereoisomers of these imidazoquinoles derivatives, or combinations thereof, have surprising and particularly advantageous properties.

The present invention provides compounds of formula I:

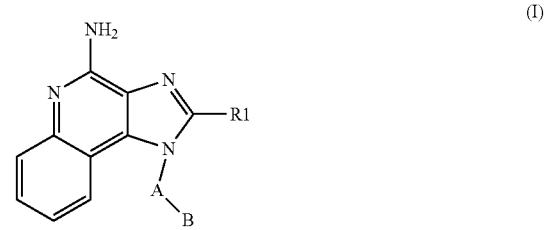

(I)

wherein $R_1$ is selected from the group consisting of:
—H, alkyl, alkynyl, aryl, alkoxy, heterocyclyl and heteroaryl,
wherein alkyl, alkynyl, aryl, alkoxy, heterocyclyl or heteroaryl may be optionally substituted by one or more groups,
which are, e.g. selected from the group consisting of:
—H, —OH, halogen, —CO—N($R_4$)$_2$, —N($R_4$)$_2$, —CO—$C_{1-10}$ alkyl, —CO—O—$C_{1-10}$ alkyl, —N$_3$, optionally substituted aryl, heterocyclyl, or —CO-aryl;
each $R_4$ is independently selected from the group consisting of:
—H, —$C_{1-10}$ alkyl, —$C_{1-10}$ alkyl-aryl, aryl;
A is $C_1$-$C_6$ alkyl;
B is —N($R_2$)($R_3$);
$R_2$ is hydrogen or —(CO)—$R_5$;
$R_5$ is selected from the group consisting of:
alkyl, alkynyl, aryl, heterocyclyl and heteroaryl, each of which may be optionally substituted by one or more groups,
which are, e.g. selected from the group consisting of:
—H, —OH, halogen, —CN, —NO$_2$, —COOH, —SH, —CO—$C_{1-6}$ alkyl, —CO—O—$C_{1-6}$ alkyl, —N$_3$, optionally substituted aryl, heterocyclyl, —CO-aryl or —CO-heterocyclyl;
$R_3$ is selected from the group consisting of:
—H, alkyl, alkenyl, aryl, heteroaryl, cycloalkyl and heterocyclyl, wherein alkyl, alkenyl, aryl, heteroaryl, cycloalkyl, or heterocyclyl may be unsubstituted or substituted by one or more substituents, which are e.g. selected from group consisting of: —H, alkyl, alkenyl, alkoxy, halogen, —OH, —N₃, triflurom-ethyl, -alkyl-aryl, —O-alkyl-aryl, —CO-aryl, aryl, heterocyclyl, heteroaryl, —CO-heteroaryl, —CO-substituted aryl, —CO— substituted heteroaryl, —CO—O-alkyl, —CO—N-alkyl, —CO—N-aryl;

or pharmaceutically acceptable solvates, salts, N-oxides or stereoisomers thereof, or combinations thereof.

As used herein, the terms "alkyl", "alkenyl", "alkynyl" and the prefix "alk" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl and adamantyl.

In particular, the term "alkyl" refers to a straight chain or branched alkyl radical having 1 to 4 carbon atoms. Examples include methyl, ethyl, propyl, isopropyl, butyl, isobutyl, sec-butyl, ter-butyl. Substituted alkyl is as defined above.

Further, the term "alkynyl" refers to an alkyl group having at least two carbon atoms and including a carbon-carbon triple bond. Substituted alkynyl is as defined above.

Likewise, "alkenyl" refers to an alkyl group having at least two carbon atoms and including a carbon-carbon double bond.

Further, the term "alkoxy" refers to an alkyl group being bonded via an oxygen atom.

The term "aryl" as used herein includes carbocyclic aromatic rings or ring systems. Examples of aryl groups include phenyl, naphthyl, biphenyl, fluorenyl and indenyl. In particular, the term "aryl" refers to phenyl or naphthalene. In a preferred embodiment, aryl is phenyl. Substituted aryl is as defined above.

The term "heteroaryl" includes aromatic rings or ring systems that contain at least one ring heteroatom (e.g. O, S, N). In particular, exemplary heteroaryl groups include furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, thiadiazolyl, pyridyl, pyridazinyl, pyrimidinyl, benzofuranyl, isobenzofuranyl, thionaphthenyl, isothion-aphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, which in each case is unsubstituted or may optionally be substituted in one or more places.

Substituted heteroaryl is substituted, e.g. by one or more of halogen, hydroxyl, aryl, alkyl, aralkyl, alkoxy, carboxy, cyano, trifluoromethyl, nitro, amino, alkylamino, dialkylamino, or combinations thereof.

As used herein, the term "heterocyclyl" refers to non-aromatic rings or mono- or bicyclic ring systems that contain at least one ring heteroatom (e.g., preferably selected from O, $SO_x$ or N, wherein x=0, 1 or 2). Exemplary heterocyclic groups include pyrrolidinyl, tetrahydrofuranyl, morpholinyl, thiomorpholinyl, piperidinyl, piperazinyl, thiazolidinyl, imidazolidinyl, tetrahydropyranyl, azabicyclooctanyl, such as 1-azabicyclo[2.2.2]-octanyl, 1-oxo and dioxo-tetrahydrothiophenyl or cyclopentylsulfonyl, as well as benzocondensed forms and/or n-oxides thereof, which in each case are unsubstituted or may optionally be substituted in one or more places. Substituted heterocyclyl is, e.g. substituted by one or more of halogen, hydroxyl, aryl, alkyl, aralkyl, alkoxy, carboxy, cyano, trifluoromethyl, nitro, amino, alkylamino, dialkylamino, or combinations thereof.

It is to be understood that the invention covers all combinations of substituent groups referred to hereinabove. In particular, the invention covers all combinations of preferred groups described hereinabove.

Pharmaceutically acceptable salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, citrates, D-gluconates, benzoates, 2-(4-hydroxybenzoyl)benzoates, butyrates, sulfosalicylates, maleates, laurates, malates, fumarates, succinates, oxalates, tartarates, stearates, toluenesulfonates, methanesulfonates, 3-hydroxy-2-naphthoates and trifluoroacetates.

Examples of salts with bases include, but are not limited to, lithium, sodium, potassium, calcium, aluminum, magnesium, titanium, ammonium, meglumine and guanidinium salts. Of these, sodium and ammonium salts are preferred.

The salts include water-insoluble and, particularly, water-soluble salts.

The compounds of the invention and the salts thereof may contain, e.g. when isolated in crystalline form, varying amounts of solvents. Included within the scope of the invention are, therefore, all solvates of the compounds of formula (I) and the salts thereof. Hydrates are a preferred example of said solvates.

N-oxides of the compounds according to the invention and the salts thereof include compounds, wherein a nitrogen atom of a substituent moiety is oxidized.

In certain embodiments, the compounds according to the invention and the salts thereof may include stereoisomers. Each of the stereogenic centers present in said stereoisomers may have the absolute configuration R or the absolute configuration S (according to the rules of Cahn, Ingold and Prelog). All such stereoisomers and the salts thereof are part of the invention. The invention further includes all mixtures of the stereoisomers mentioned above independent of the ratio, including the racemates.

Compounds of the invention and salts thereof containing a double bond may exist as E isomers and Z isomers. Both said isomers are included in the invention. The Z isomer is the geometric isomer in which the carbon atoms connected by the double bond each have the two highest ranking groups on the same side of the double bond. The E isomer is the geometric isomer in which the carbon atoms connected by the double bond each have the two highest ranking groups on opposite sides of the double bond.

Some of the compounds and salts according to the invention may exist in different crystalline forms (polymorphs) which are within the scope of the invention.

Furthermore, derivatives of the compounds of formula (I) and the salts thereof which are converted into compound (I) or a salt thereof in a biological system (bioprecursors or pro-drugs) are covered by the invention. Said biological system is, e.g. a mammalian organism, particularly a human subject. The bioprecursor is, for example, converted into the compound of formula (I) or a salt thereof by a metabolic process.

According to one preferred embodiment of the present invention, compounds of formula I in which $R_1$ is —H, alkyl, optionally substituted aryl, heterocyclyl, or optionally substituted heteroaryl; $R_2$ is —(CO)—$R_5$, wherein $R_5$ is alkyl, aryl, or heteroaryl, and $R_3$ is —H, or alkyl, are excluded from the present invention.

In another preferred embodiment, the present invention relates to a compound of formula Ia, which is a compound of formula I as defined above, wherein $R_2$ is hydrogen.

In another preferred embodiment, the present invention relates to a compound of formula Ib, which is a compound of formula I as defined above, wherein $R_2$ is —(CO)—$R_5$; and $R_3$ is selected from groups consisting of: alkenyl, aryl, heteroaryl, cycloalkyl and heterocyclyl, each of which may be unsubstituted or substituted by one or more substituents.

In another preferred embodiment, the present invention relates to a compound of formula Ic, which is a compound of formula I as defined above, wherein $R_1$ is alkynyl or alkoxy; and $R_2$ is —(CO)—$R_5$.

In a preferred embodiment of the compound of formula I, including the compounds of formula Ia, Ib and Ic, according to the present invention, $R_3$ is heterocyclyl, which may be unsubstituted or substituted by one or more substituents, as defined above.

In another preferred embodiment of the compound of formula I, including the compounds of formula Ia, Ib and Ic, $R_1$ is alkyl, more preferably ethyl.

In another preferred embodiment of the compound of formula I, including the compounds of formula Ia, Ib and Ic, $R_5$ is alkyl, more preferably methyl.

In another preferred embodiment of the compound of formula I, including the compounds of formula Ia, Ib and Ic, $R_3$ is heterocyclyl, which may be unsubstituted or substituted by one or more substituents selected from group consisting of: hydrogen, alkyl, alkenyl, halogen, or —OH.

In another preferred embodiment of the compound of formula I, including the compounds of formula Ia, Ib and Ic, A is $C_{2-4}$ alkyl, more preferably $C_4$ alkyl.

Another preferred embodiment of the compounds according to the present invention relates to compounds of formula I selected from:

N-[4-(4-amino-2-ethyl-1H-imidazo[4,5-c]quinolin-1-yl)butyl]-N-(1,1-dioxidotetrahydro-3-thienyl) acetamide, N-[4-(4-amino-2-ethyl-1H-imidazo[4,5-c]quinolin-1-yl)butyl]-N-(1-methyl-1-oxidopiperidin-4-yl)acetamide, 3-{acetyl[4-(4-amino-2-ethyl-1H-imidazo[4,5-c]quinolin-1-yl)butyl]amino}-2,5-anhydro-1,3,4-trideoxypentitol, N-[4-(4-amino-2-ethyl-1H-imidazo[4,5-c]quinolin-1-yl)butyl]-N-(1-benzyl-2-methyl-1-oxidopyrrolidin-3-yl)acetamide, 2-ethyl-1-[4-(tetrahydro-2H-pyran-4-ylamino)butyl]-1H-imidazo[4,5-c]quinolin-4-amine, 1-[4-(1-azabicyclo[2.2.2]oct-3-ylamino)butyl]-2-ethyl-1H-imidazo[4,5-c]quinolin-4-amine or 1-{4-[(1,1-dioxido-3,4-dihydro-2H-thiochromen-4-yl)amino]butyl}-2-ethyl-1H-imidazo[4,5-c]quinolin-4-amine or pharmaceutically acceptable solvates, salts, N-oxides or stereoisomers thereof, or combinations thereof.

Pharmaceutical compositions of the invention contain a therapeutically effective amount of a compound of formula I (including formula Ia, Ib and Ic) according to the present invention in combination with a pharmaceutically acceptable carrier.

The term "therapeutically effective amount" means an amount of the compound sufficient to induce a therapeutic effect, such as activation of TLR7. This may cause cytokine induction, antitumor activity and/or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50 mg/kg, preferably about 10 µg/kg to about 5 mg/kg, of the compound to the subject.

Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in a treatment regimen, or may be administered in combination with one another or with other active agents, including additional anticancer agents, immune response modifiers, antivirals, antibiotics, and the like.

The invention furthermore relates to pharmaceutical compositions which comprise at least one of the compounds and pharmaceutically acceptable salts according to the invention together with at least one pharmaceutically acceptable auxiliary.

Preferably, the pharmaceutical compositions comprise one or two of the compounds and pharmaceutically acceptable salts according to the invention. More preferably, the pharmaceutical compositions comprise one of the compounds and pharmaceutically acceptable salts according to the invention.

In a particularly preferred embodiment of the invention, the pharmaceutical compositions comprise a compound of the examples according to the invention together with at least one pharmaceutically acceptable auxiliary.

The pharmaceutical compositions can contain at least one of the compounds and pharmaceutically acceptable salts according to the invention (hereinafter referred to as "the active compound") in a total amount of from 0.1 to 99.9 wt %, preferably 5 to 95 wt %, more preferably 20 to 80 wt %.

As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions can be formulated, for example, into tablets, coated tablets (dragées), pills, cachets, capsules (caplets), granules, powders, suppositories, solutions (e.g. sterile solutions), emulsions, suspensions, ointments, creams, lotions, pastes, oils, gels, sprays and patches (e.g. transdermal therapeutic systems). Additionally, the pharmaceutical compositions can be prepared as, e.g. liposome delivery systems, systems in which the active compound is coupled to monoclonal antibodies and systems in which the active compound is coupled to polymers (e.g. soluble or biodegradable polymers).

The pharmaceutical compositions comprising the active compound and at least one auxiliary can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the invention can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration is preferred.

Tablets, coated tablets (dragees), pills, cachets, capsules (caplets), granules, solutions, emulsions and suspensions are, e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the active compound to be administered, the aerosol-producing device can contain the active compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 μm, in particular in the range of from 2 to 6 μm (ID50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g. transdermal therapeutic systems).

For parenteral modes of administration such as, for example, intravenous, intraarterial, intramuscular, subcutaneous, intracutaneous, intraperitoneal and intrasternal administration, preferably solutions (e.g. sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the invention can be administered such that the dose of the active compound is in the range customary for activators of TLR7. In particular, a dose in the range of from 0.01 to 4000 mg, preferably 0.1 mg to 2000 mg, more preferably 0.5 mg to 1000 mg and most preferably 1 mg to 500 mg, of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain, e.g. from 0.01 mg to 4000 mg, preferably 0.1 mg to 2000 mg, more preferably 0.5 to 1000 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The compounds of the invention have been shown to activate TLR7 in experiments performed according to the tests set forth below. The compounds of the present invention are useful as anticancer agents for cancers that are responsive to TLR7 activation.

Illustrative cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

Preferably, TLR7 agonists would be used to treat cancers of the skin or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hopitalization, altered hemogram, weight loss, wound healing, fever).

The compounds according to the present invention may further be useful as immune response modifiers that can modulate the immune response in a number of different ways, rendering them useful in the treatment of a variety of disorders.

Cytokines that may be induced by the administration of compounds according to the invention generally include interferon (IFN) and/or tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of tumors and viral diseases.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention may also have an effect on the acquired immune response. For example, while not intending to be bound by any particular theory, there is not believed to be any direct effect on T cells or direct induction of T cell cytokines, but the production of the T helper type 1 (Th 1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where up-regulation of the Th1 response and/or down regulation of the Th2 response is desired. In view of the ability of certain compounds of Formula I to inhibit the Th2 immune response, the compounds are expected to be useful in the treatment of conditions that are associate with overstimulation of a Th2 response such as atopic diseases, e.g., atopic dermatitis; asthma; allergy; allergic rhinitis; systemic lupus erythematosis; as a vaccine adjuvant for cell mediated immunity; and possibly as a treatment for recurrent fungal diseases, periodontitis and chlamydia.

The immune response modifying effects of the compounds make them useful in the treatment of a wide variety of conditions. Because of their ability to induce the production of cytokines such as IFN-α and/or TNF-α, and IL-12, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. *pneumocystis carnii*, cryptosporidiosis, histoplasmosis, toxoplasmosis, trypanosome infection, and leishmaniasis; and bacterial infections, e.g., tuberculosis, and *mycobacterium avium*. Additional diseases or conditions that can be treated using the compounds of the invention include eczema; eosinophilia; essential thrombocythaemia; leprosy; multiple sclerosis; Ommen's syndrome; discoid lupus; Bowen's disease; Bowenoid papulosis; and to enhance or stimulate the healing of wounds, including chronic wounds.

Accordingly, the invention provides a method of activating TLR7 in an animal, especially a mammal, preferably a human comprising administering an effective amount of a compound of Formula I to the animal. An effective amount of a compound will vary according to factors known in the art but is expected to be a dose of about 100 ng/kg to about 60 mg/kg, preferably about 10 µg/kg to about 30 mg/kg, more preferably about 10 µg/kg to about 5 mg/kg.

The invention also provides a method of treating a viral infection in an animal comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, preferably about 10 µg/kg to about 5 mg/kg.

An amount effective to treat a neoplastic condition is an amount that will cause a reduction in tumor size or in the number of tumor foci. Again, the precise amount will vary according to factors known in the art but is expected to be a dose as indicated above with respect to the activation of TLR7, or a dose of about 100 mg/kg to about 50 mg/kg, preferably about 10 mg/kg to about 5 mg/kg.

The compounds according to the invention can be prepared, for example, as described as follows and according to the following specified reaction steps, or, particularly, in a manner as described by way of example in the following examples.

As shown in reaction scheme A, a compound of formula 7 wherein $R_3$ is having meaning as defined above can be obtained by treating quinolin-4-ol with nitric acid to afford its nitro derivative of formula 1 which is further reacted with phosphorus oxychloride in presence of N,N-dimethyl formaldehyde to yield 4-chloro-3-nitroquinoline of formula 2. Compound of formula 2 on reaction with (4-Amino-butyl)-carbamic acid tert-butylester resulted in compound of formula 4 which is then reacted with triethylorthopropionate in presence of toluene to afford compound of formula 5. [4-(2-Ethyl-imidazo[4,5-c]quinolin-1-yl)-butyl]-carbamic acid tert-butyl ester of formula 5 is then deprotected to afford 4-(2-Ethyl-imidazo[4,5-c]quinolin-1-yl)-butylamine of formula 6. A compound of formula 6 is then treated with suitable heterocyclic ketones to obtain a desired compound of formula 7.

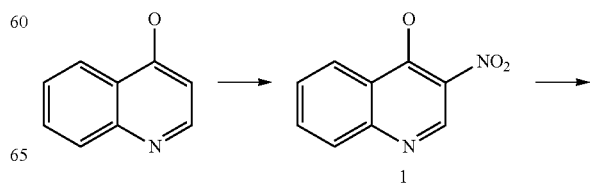

Scheme A

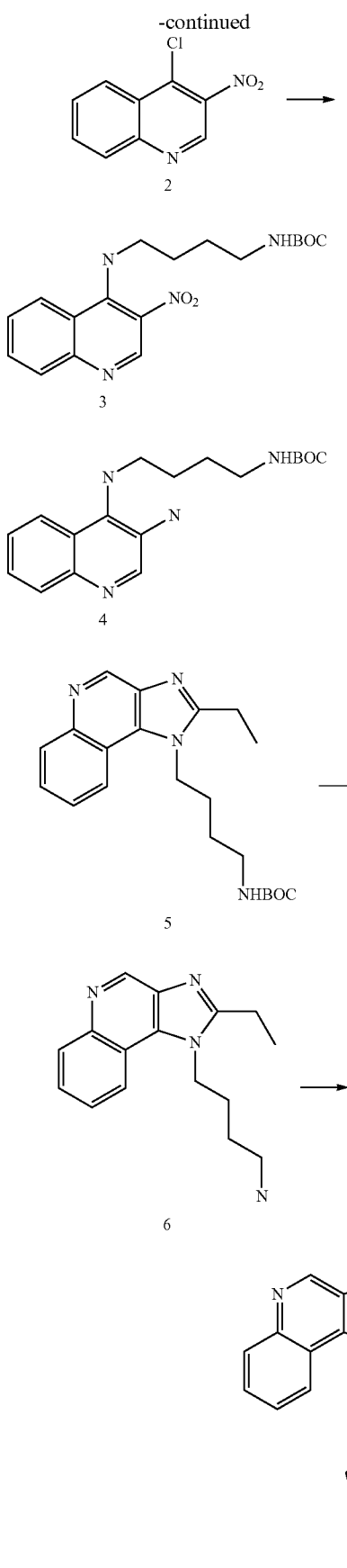

As shown in reaction scheme B, compound of formula I, wherein $R_2$ is —CO—$R_5$ and all other symbols have the meaning as defined above, can be obtained by reacting compound of formula 7 with suitable acid anhydride of formula $R_5$—CO—O—CO—$R_5$ to obtain a compound of formula 8 which is then treated with m-chloroperbenzoic acid to yield its N-oxide derivative of formula 9. A compound of formula 9 is further subjected to amination using aqueous (aq.) ammonia solution to obtain the desired compound of formula I.

Scheme B

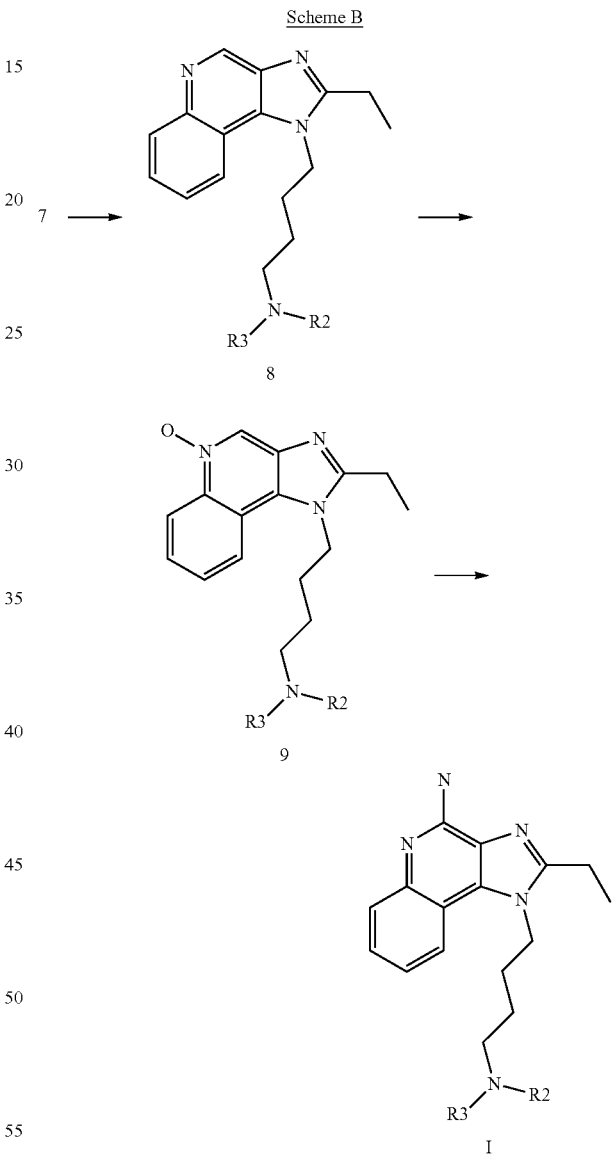

As shown in reaction scheme C, a compound of formula I, wherein $R_2$ is hydrogen and all other symbols have the meaning as defined above, can be obtained by reacting compound of formula 7 with di-ter-butyl-dicarbonate to obtain a compound of formula 10, which is then treated with m-chloroperbonzoic acid to yield its N-oxide derivative of formula 11. Compound of formula 11 is then further subjected to amination using aq.ammonia to obtain a compound of formula 12 which is the deprotected using acidic conditions to obtain the desired compound of formula I.

Scheme C

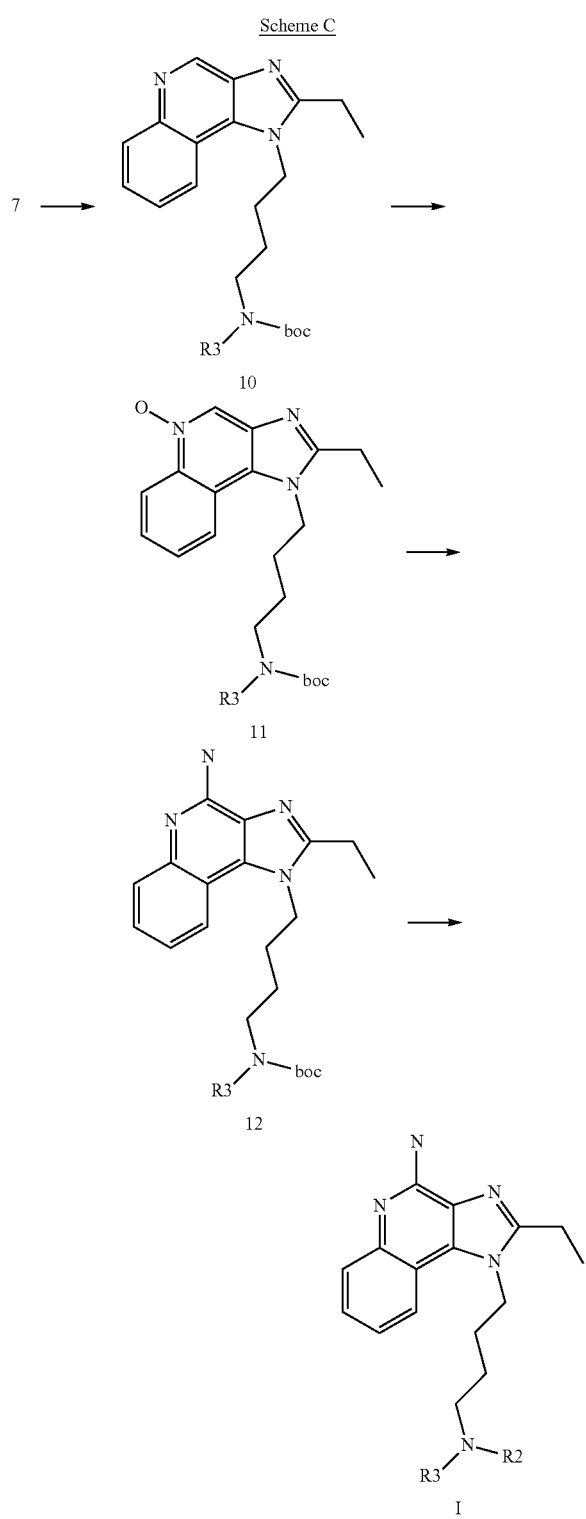

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the invention are isolated and purified in a manner known per se, e.g. by distilling off the solvent in vaccuo and recrystallizing the residue obtained from a suitable solvent or subjecting it to one of the customary purification methods, such as column chromatography on a suitable support material.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

The compounds of formula (I) according to the invention can be converted into their N-oxides, for example, with the aid of hydrogen peroxide in methanol or with the aid of m-chloroperoxybenzoic acid in dichloromethane. The person skilled in the art is familiar with the reaction conditions for carrying out the N-oxidation.

Pure diastereomers and pure enantiomers of the compounds and salts according to the invention that are present in the form of such stereoisomers can be obtained, e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds which are mentioned in the examples and the salts thereof represent preferred embodiments of the invention.

EXAMPLES

Preparation of
4-(2-Ethyl-imidazo[4,5-c]quinolin-1-yl)-butylamine
of formula 6

Step-I: 3-Nitro-quinoline-4-ol

A mixture of quinolin-4-ol (1 eq.) in propionic acid was heated to 125° C. with stirring. Nitric acid (2.2 eq.) was added drop wise to the stirred solution while maintaining the reaction mixture temperature at 125° C. Reaction was stirred at 125° C. for 15 min. and cooled to ambient temperature. The reaction was diluted with ethanol and solid was collected by vacuum filtration. Solid was washed successively with ethanol, water and ethanol. Resulting yellow solid was heated in refluxing ethanol and filtered from hot mixture to give pure 3-nitro-quinoline-4-ol.

Step-II: 4-Chloro-3-nitro-quinoline

Phosphorus oxychloride (1.2 eq.) was added slowly to well stirred suspension of compound of formula 1 obtained in step I in N, N-dimethylformamide. The reaction mixture was further heated to 50° C. with stirring for 30 min. The resulting solution was cooled at ambient temperature and poured into an ice/water mixture. A solid was collected by filtration and dried to afford 4-chloro-3-nitro-quinoline.

Step-III: tert-butyl {4-[(3-nitroquinolin-4-yl)amino]butyl}carbamate

A compound of formula 2 (1 eq.) was added to a solution of (4-Amino-butyl)-carbamic acid tert-butylester (1.2 eq.) and triethyl amine (1.5 eq.) in ethanol. Reaction mixture was then refluxed for 15 min and then diluted with water to precipitate impure product, which was separated by filtration. Saturated ammonium hydroxide solution was added to filtrate and precipitated solid was collected by vacuum filtration and dried to yield tert-butyl {4-[(3-nitroquinolin-4-yl)amino]butyl}carbamate of formula 3.

Step-IV: tert-butyl {4-[(3-aminoquinolin-4-yl)amino]butyl}carbamate

A suspension of compound of compound of formula 3 (1 eq.), 5% palladium on carbon (2% by wt.) and magnesium sulphate in ethyl acetate was hydrogenated on a parr apparatus at 50 psi of hydrogen gas for 4 hrs. The resulting reaction mixture was then filtered and filtrate was concentrated at reduced pressure to yield crude solid, which then purified by silica gel column chromatography to afford tert-butyl {4-[(3-aminoquinolin-4-yl)amino]butyl}carbamate of formula 4.

Step-V: tert-butyl[4-(2-ethyl-1H-imidazo[4,5-c]quinolin-1-yl)butyl]carbamate

To a solution of compound of formula 4 (1 eq.) in toluene was added triethylorthopropionate (2 eq.) and resulting reaction mixture was heated at 80-90° C. for 5 hrs. Reaction mixture was then cooled and solvent was evaporated to remove 50% of toluene. To a remaining reaction mixture was added ice-water and product was precipitated as white solid which was then separated by vacuum filtration and dried to afford tert-butyl[4-(2-ethyl-1H-imidazo[4,5-c]quinolin-1-yl)butyl]carbamate of formula 5.

Step-VI: 4-(2-ethyl-1H-imidazo[4,5-c]quinolin-1-yl)butan-1-amine

A solution of [4-(2-Ethyl-imidazo[4,5-c]quinolin-1-yl)-butyl]carbamic acid tert-butyl ester of formula 5 obtained in step V in trifluroacetic acid was stirred at 40° C. for 4 hrs. Reaction mixture was then poured on ice-water mixture and extracted with chloroform. Organic layer was dried over sodium sulphate and concentrated under deduced pressure to afford 4-(2-ethyl-1H-imidazo[4,5-c]quinolin-1-yl) butan-1-amine of formula 6.

Example I

N-[4-(4-amino-2-ethyl-1H-imidazo[4,5-c]quinolin-1-yl)butyl]-N-(1,1-dioxidotetrahydro-3-thienyl)acetamide Step-I: N-[4-(2-ethyl-1H-imidazo[4,5-c]quinolin-1-yl)butyl]tetrahydrothiophen-3-amine To a suspension of 4-(2-Ethyl-imidazo[4,5-c]quinolin-1-yl)-butylamine obtained in step VI in tetrahydrofuran was added acetic acid (1 eq.) and dihydrothiophen-3-one (1.1 eq.). Resulting reaction mixture was stirred for 10 min. Sodium triacetoxyborohydride (2.2 eq.) was added to reaction mixture over a period of 1 hrs and resulting suspension was then stirred for 4-5 hrs. Reaction was then quenched with methanol and concentrated to dryness. Reaction mixture was basified using aq.sodium hydroxide solution and extracted with chloroform. Organic layer was dried over sodium sulphate and concentrated under reduced pressure to yield sticky solid. Product was then purified by silica gel column chromatography to afford [4-(2-Ethyl-imidazo[4,5-c]quinolin-1-yl)-butyl]-(tetrahydro-thiophen-3-yl)-amine.

Step-II: N-[4-(2-ethyl-1H-imidazo[4,5-c]quinolin-1-yl)butyl]-(tetrahydro-3-thienyl)acetamide To a solution of [4-(2-Ethyl-imidazo[4,5-c]quinolin-1-yl)-butyl]-(tetrahydro-thiophen-3-yl)-amine in dichloromethane was added triethyl amine (1.5 eq.) and acetic anhydride (1.5 eq.) and stirred at ambient temperature for 4 hrs. Reaction mixture was then diluted with dichloromethane and washed with saturated sodium bicarbonate solution. Organic layer was dried over sodium sulphate and concentrated under reduced pressure to afford N-[4-(2-ethyl-1H-imidazo[4,5-c]quinolin-1-yl)butyl]-N-(tetrahydro-3-thienyl) acetamide.

Step-III: N-(1,1-dioxidotetrahydro-3-thienyl)-N-[4-(2-ethyl-5-oxido-1H-imidazo[4,5-c]quinolin-1-yl)butyl]acetamide To a solution of N-[4-(2-Ethyl-imidazo[4,5-c]quinolin-1-yl)-butyl]-(tetrahydro-thiophen-3-yl)-acetamide in chloroform was added m-chloroperbenzoic acid (4 eq.) and stirred at ambient temperature for 2 hrs. Reaction mixture was then diluted with chloroform and washed with saturated sodium bicarbonate solution. Organic layer was dried over sodium sulphate and concentrated under reduced pressure to yield sticky mass. Product was then purified using silica gel column chromatography to afford N-(1,1-dioxidotetrahydro-3-thienyl)-N-[4-(2-ethyl-5-oxido-1H-imidazo[4,5-c]quinolin-1-yl)butyl]acetamide.

Step-IV: N-[4-(4-amino-2-ethyl-1H-imidazo[4,5-c]quinolin-1-yl)butyl]-N-(1,1-dioxidotetrahydro-3-thienyl) acetamide To a solution of (1,1-Dioxo-tetrahydro-1lambda*6*-thiophen-3-yl)-N-[4-(2-ethyl-5-oxy-imidazo[4,5-c]quinolin-1-yl)-butyl]acetamide in chloroform was added p-toluene sulfonyl chloride (1.2 eq.) followed by aq.ammonium hydroxide solution. The resulting reaction mixture was stirred at room temperature for overnight. Reaction mixture was then diluted with chloroform and washed with saturated sodium bicarbonate solution. Organic layer was dried over sodium sulphate and concentrated under reduced pressure to yield sticky solid, which was then purified using silica gel column chromatography to afford the title compound.

$^1$H NMR (300 MHz, CDCl$_3$) δ (ppm): 8.29 (dd, 1H, J=8.4 & J=3.0 Hz), 8.21 (dd, 1H, J=8.4 Hz, J=3.0 Hz), 7.65 (m, 2H), 5.49 (s, 2H), 4.58 (t, 2H), 3.78 (t, 2H), 3.3 (t, 2H), 3.02 (q, 2H), 2.34 (d, 2H), 2.2 (t, 1H), 2.1 (s, 3H), 2.09 (m, 2H), 1.9 (m, 2H), 1.79 (m, 2H), 1.55 (t, 3H)

Examples 2-4 were also prepared by following procedure of example I.

Example II

N-[4-(4-amino-2-ethyl-1H-imidazo[4,5-c]quinolin-1-yl)butyl]-N-(1-methyl-1-oxidopiperidin-4-yl) acetamide $^1$H NMR (300 MHz, CDCl$_3$) δ (ppm): 8.24 (dd, 1H, J=8.4 & J=3.0 Hz), 8.19 (dd, 1H, J=8.4&J=3.0 Hz), 7.60 (m, 2H), 5.60 (s, 2H), 4.52 (t, 2H), 3.75 (t, 2H), 3.4 (m, 1H), 3.2 (m, 4H), 3.12 (q, 2H), 2.16 (s, 3H), 2.01 (m, 2H), 1.99 (m, 4H), 1.70 (m, 2H), 1.51 (t, 3H)

Example III

3-{acetyl[4-(4-amino-2-ethyl-1H-imidazo[4,5-c]quinolin-1-yl)butyl]amino}-2,5-anhydro-1,3,4-trideoxypentitol $^1$H NMR (300 MHz, CDCl$_3$) δ (ppm): 8.35 (dd, 1H, J=8.4 & J=3.0 Hz), 8.29 (dd, 1H, J=8.4&J=3.0 Hz), 7.63 (m, 2H), 5.56 (s, 2H), 4.50 (t, 2H), 4.42 (m, 1H), 3.70 (t, 2H), 3.62 (m, 1H), 3.35 (t, 2H), 3.12 (q, 2H), 2.15 (s, 3H), 2.05 (m, 2H), 1.92 (d, 3H), 1.8 (t, 2H) 1.70 (m, 2H), 1.51 (t, 3H)

Example IV

N-[4-(4-amino-2-ethyl-1H-imidazo[4,5-c]quinolin-1-yl)butyl]-N-(1-benzyl-2-methyl-1-oxidopyrrolidin-3-yl)acetamide $^1$H NMR (300 MHz, CDCl$_3$) δ (ppm): 8.31 (dd, 1H, J=8.4 & J=3.0 Hz), 8.15 (dd, 1H, J=8.4 Hz, J=3.0 Hz), 7.62 (m, 2H), 7.55 (m, 5H), 5.59 (s, 2H), 4.50 (t, 2H), 3.71 (t, 2H), 3.35 (t, 2H), 3.23 (s, 2H), 3.21 (q, 2H), 2.19 (d, 2H), 2.15 (t, 1H), 2.10 (s, 3H), 2.09 (m, 2H), 1.9 (m, 2H), 1.79 (m, 2H), 1.55 (t, 3H).

Example V

2-ethyl-1-[4-(tetrahydro-2H-pyran-4-ylamino)butyl]-1H-imidazo[4,5-c]quinolin-4-amine

Step-I: N-[4-(2-ethyl-1H-imidazo[4,5-c]quinolin-1-yl)butyl]tetrahydro-2H-pyran-4-amine To a suspension of 4-(2-ethyl-1H-imidazo[4,5-c]quinolin-1-yl) butan-1-amine obtained in step VI of example I in tetrahydrofuran was added acetic acid (1 eq.) and tetrahydropyran-4-one (1.1 eq.). Resulting reaction mixture was stirred for 10 min. Sodium triacetoxyborohydride (2.2 eq.) was added to reaction mixture over a period of 1 hrs and resulting suspension was then stirred for 4-5 hrs. Reaction was then quenched with methanol and concentrated to dryness. Reaction mixture was basified using aq.sodium hydroxide solution and extracted with chloroform. Organic layer was dried over sodium sulphate and concentrated under reduced pressure to yield sticky solid. Product was then purified by silica gel column chromatography to afford N-[4-(2-ethyl-1H-imidazo[4,5-c]quinolin-1-yl)butyl]tetrahydro-2H-pyran-4-amine.

Step-II: tert-butyl[4-(2-ethyl-1H-imidazo[4,5-c]quinolin-1-yl)butyl]tetrahydro-2H-pyran-4-ylcarbamate To a solution of N-[4-(2-ethyl-1H-imidazo[4,5-c]quinolin-1-yl)butyl]tetrahydro-2H-pyran-4-amine in dichloromethane was added triethyl amine (1.5 eq.) followed by di-ter-butyl-dicarbonate (1.5 eq.) and resulting reaction mixture was stirred for 4 hrs at ambient temperature. Reaction mixture was then evaporated completely and dissolved in dichloromethane, washed with water and organic layer was dried over sodium sulfate and concentrated under reduced pressure to afford tert-butyl[4-(2-ethyl-1H-imidazo[4,5-c]quinolin-1-yl)butyl]tetrahydro-2H-pyran-4-ylcarbamate.

Step-III: tert-butyl[4-(2-ethyl-5-oxido-1H-imidazo[4,5-c]quinolin-1-yl)butyl]tetrahydro-2H-pyran-4-ylcarbamate To a solution of tert-butyl[4-(2-ethyl-1H-imidazo[4,5-c]quinolin-1-yl)butyl]tetrahydro-2H-pyran-4-ylcarbamate in chloroform was added m-chloroperbenzoic acid (4 eq.) and stirred at ambient temperature for 2 hrs. Reaction mixture was then diluted with chloroform and washed with saturated sodium bicarbonate solution. Organic layer was dried over sodium sulphate and concentrated under reduced pressure to yield sticky mass. Product was then purified using silica gel column chromatography to afford tert-butyl[4-(2-ethyl-5-oxido-1H-imidazo[4,5-c]quinolin-1-yl)butyl]tetrahydro-2H-pyran-4-ylcarbamate.

Step-IV: tert-butyl[4-(4-amino-2-ethyl-1H-imidazo[4,5-c]quinolin-1-yl)butyl]tetrahydro-2H-pyran-4-ylcarbamate To a solution of tert-butyl[4-(2-ethyl-5-oxido-1H-imidazo[4,5-c]quinolin-1-yl)butyl]tetrahydro-2H-pyran-4-ylcarbamate in chloroform was added p-toluene sulfonyl chloride (1.2 eq.) followed by aq.ammonium hydroxide solution. The resulting reaction mixture was stirred at room temperature for overnight. Reaction mixture was washed with saturated sodium bicarbonate solution. Organic layer separated, dried over anhydrous sodium sulphate and concentrated under reduced pressure to yield sticky solid, which was then purified using silica gel column chromatography to afford tert-butyl[4-(4-amino-2-ethyl-1H-imidazo[4,5-c]quinolin-1-yl)butyl]tetrahydro-2H-pyran-4-ylcarbamate.

Step-V: 2-ethyl-1-[4-(tetrahydro-2H-pyran-4-ylamino)butyl]-1H-imidazo[4,5-c]quinolin-4-amine A solution of tert-butyl[4-(4-amino-2-ethyl-1H-imidazo[4,5-c]quinolin-1-yl)butyl]tetrahydro-2H-pyran-4-ylcarbamate in trifluroacetic acid was stirred at 40° C. for 4 hrs. Reaction mixture was then poured on ice-water mixture and extracted with chloroform. Organic layer was dried over sodium sulphate and concentrated under deduced pressure to afford the title compound.

$^1$H NMR (300 MHz, MeOD) δ (ppm): 8.2 (d, 1H, J=8.1 Hz), 7.75 (m, 2H), 7.6 (dt, 1H, J=1.5 & 7.2 Hz), 4.69 (t, 2H), 4.01 (d, 1H), 3.98 (d, 1H), 3.4 (m, 3H), 3.2 (m, 2H), 3.1 (m, 2H), 2.0 (m, 4H), 1.9 (m, 4H), 1.5 (t, 3H)

Examples 6-7 were also prepared by following procedure of example 5.

Example VI

1-[4-(1-azabicyclo[2.2.2]oct-3-ylamino)butyl]-2-ethyl-1H-imidazo[4,5-c]quinolin-4-amine $^1$H NMR (300 MHz, MeOD) δ (ppm): 8.01 (d, 1H, J=8.4 Hz), 7.67 (dd, 1H, J=1.2 & 8.4 Hz), 7.4 (dt, 1H, J=1.5 & 7.8 Hz), 7.33 (dt, 1H, J=1.2 & 7.5 Hz), 4.5 (m, 2H), 4.2 (m, 2H), 3.6 (m, 1H), 3.4 (m, 1H), 3.1 (m, 2H), 3.0 (q, 2H), 2.7 (m, 2H), 1.9 (m, 3H), 1.7 (m, 2H), 1.5 (t, 3H), 1.4 (m, 2H), 1.3 (m, 3H).

Example VII

1-{4-[(1,1-dioxido-3,4-dihydro-2H-thiochromen-4-yl)amino]butyl}-2-ethyl-1H-imidazo[4,5-c]quinolin-4-amine $^1$H NMR (300 MHz, MeOD) δ (ppm): 8.2 (d, 1H, J=8.1 Hz), 7.80 (dt, 1H, J=1.5 & 6.3 Hz), 7.73 (d, 1H, J=7.5 Hz), 7.64 (dt, 1H, J=1.5 & 7.5 Hz), 7.5 (m, 4H), 4.59 (t, 2H), 3.97 (t, 1H), 3.70 (m, 1H), 3.02 (q, 2H), 2.71 (m, 3H), 2.50 (m, 2H), 1.99 (m, 2H), 1.69 (m, 2H), 1.48 (t, 3H).

Example A

In Vitro Profiling

Cellular assays using a human cancer cell line (PCIR-1) or human PBMC fractions to test compounds for activating TLR7 are established.

Specificity for TLR7 and 9 was checked by adding chloroquine, which abrogates signaling through endosomal TLRs. The PCIR-1 system is suited for measuring the interferone-linked cytokine IP10 by a bead-based assay in the 384-well format.

TLR mRNA Expression in PCIR-1 (TaqMan PCR Analysis)

TLR1++, TLR2 (+), TLR3+, TLR4++, TLR5 (+), TLR6++, TLR7++, TLR8−, TLR9+++, TLR10−.

Treatment of this cell line with TLR agonist reference compounds LPS (TLR4 ago), resiquimod (imidazoquinoline) and H2006 (CpG oligonucleotide) result in strong cytokine mRNA induction. Also response to poly I-C double-stranded RNA (TLR 3 ago); 40-fold induction of IP-10 after 15 h) and MALP-2 (TLR 2/6 hetero-dimer ago, 100-fold induction of IP-10 after 15 h) is detected.

RNA induction data was confirmed by parallel Luminex analysis showing strong release of IP-10 and IL8 cytokines, in particular, and also significant protein levels of IL6, IL12p40/p70 and IL10.

The signaling via TLR7 and TLR9 (both expressed in endosomes) can be completely blocked by the addition of chloroquine, which is known to disturb the endosomal pH gradient. In contrast TLR4 signaling by LPS is not affected (FIG. 1).

Figure 2:
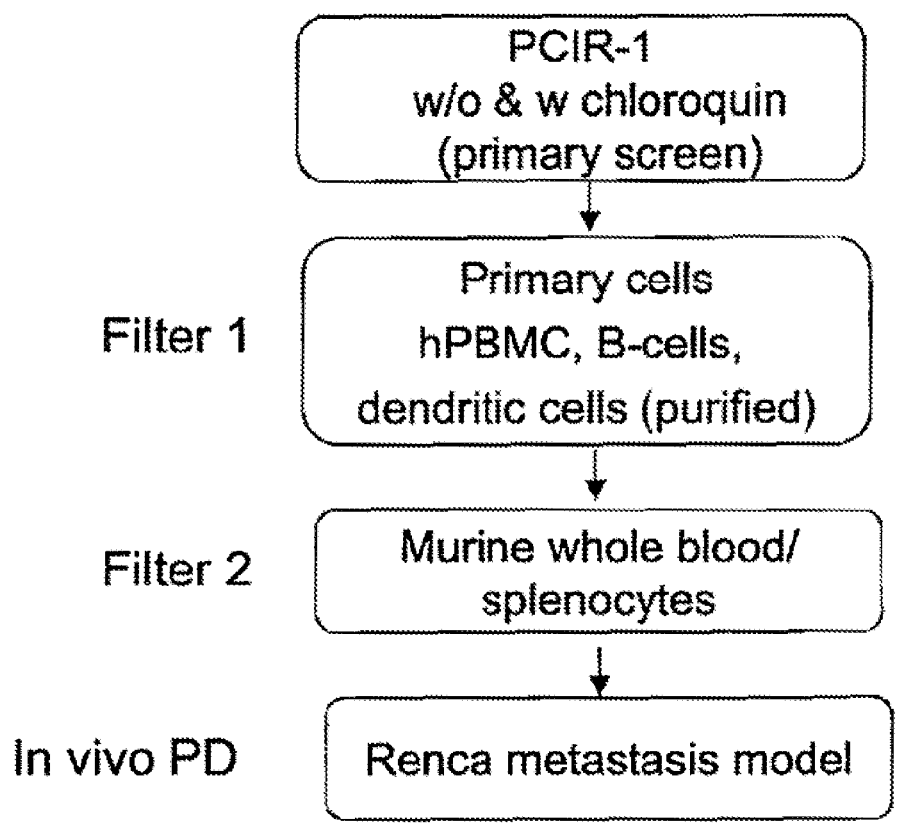
FIG. 2 shows the TLR agonist screening cascade.

The current concept for a TLR agonist-screening cascade in a high- or medium-throughput format is summarized in FIG. 2.

Figure 3A:
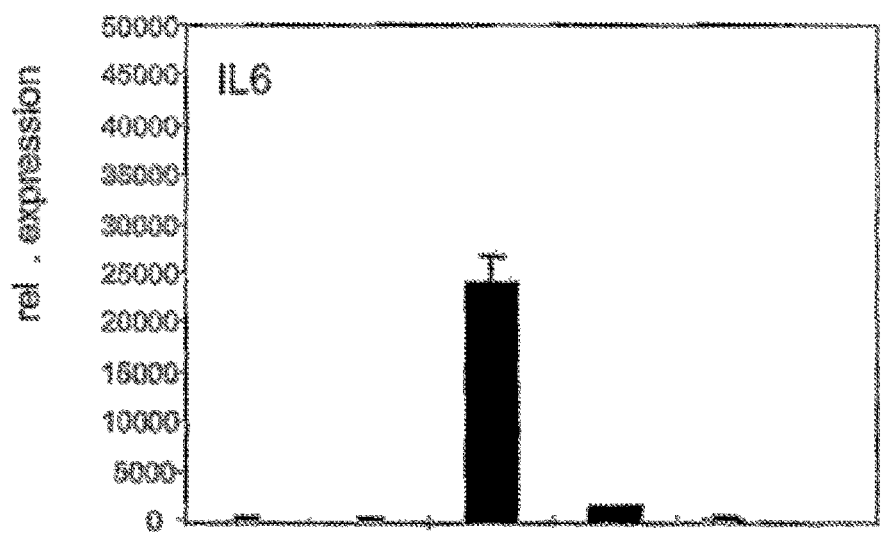
FIG. 3A shows cytokine mRNA induction in hPBMC treated with 3-{acetyl[4-(4-amino-2-ethyl-1H-imidazo[4,5-c]quinolin-1-yl)butyl]amino}-2,5-anhydro-1,3,4-trideoxypentitol (example III, TLR ago 1).
Figure 3B:
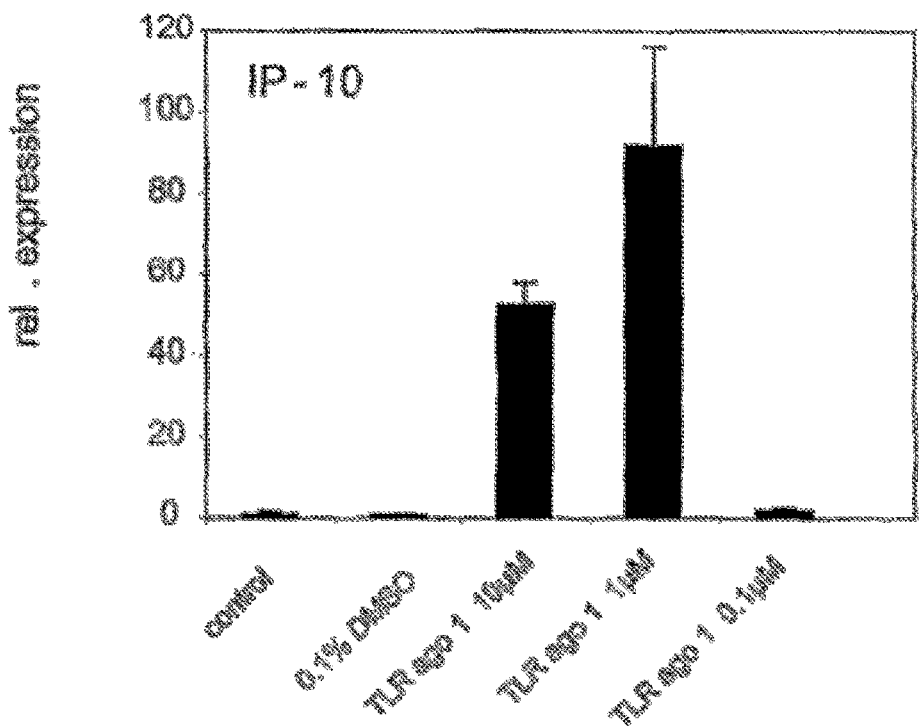
FIG. 3B shows cytokine mRNA induction in hPBMC treated with 3-{acetyl[4-(4-amino-2-ethyl-1H-imidazo[4,5-c]quinolin-1-yl)butyl]amino}-2,5-anhydro-1,3,4-trideoxypentitol (example III, TLR ago 1).

Compounds of the present invention are tested for specified cytokine induction at the mRNA or protein levels. The Compounds show efficacy in the cellular assays (FIG. 3).

Example B

In Vivo PD Profiling

In the following, studies with the reference compounds and compounds according to the invention are shown in the Renca lung metastasis model as described in Leja A, Hofmann H P, Maier T, Drache D, Grebe C, Fischer S, Gimmnich P, Sanders K, Gekeler V. Metastasis of murine Renca kidney cancer cells to the lungs of Balb/c mice is strongly suppressed by TLR9 or TLR7 agonists. Abstract 3552, Proc Am Cancer Res 48, 2007.

Figure 4A:
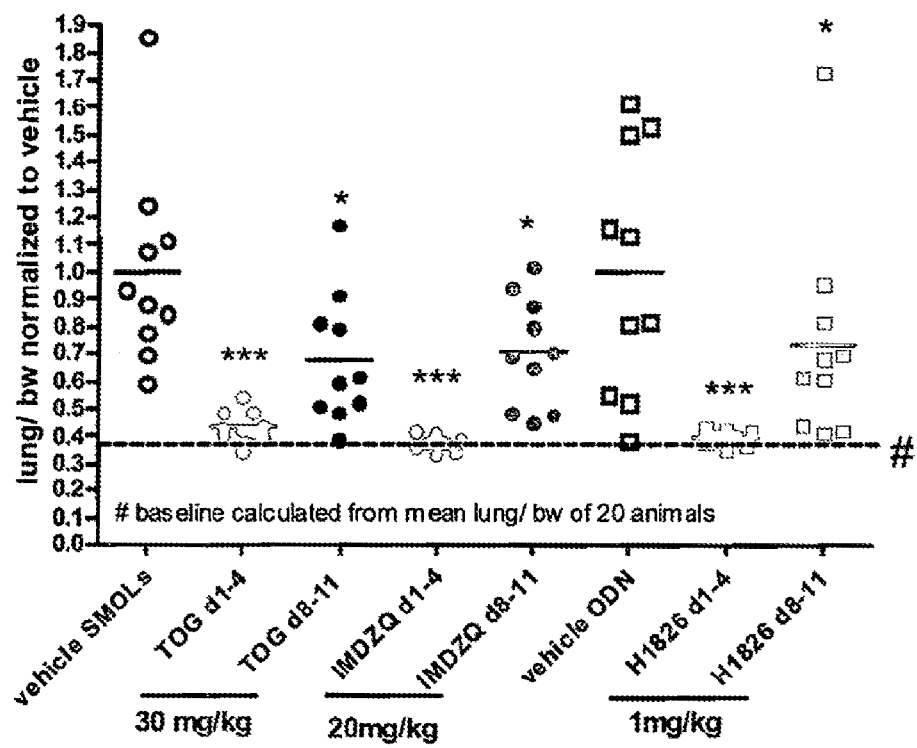
FIG. 4A shows studies with reference compounds in the Renca lung metastasis model (Leja A, Hofmann H P, Maier T, Drache D, Grebe C, Fischer S, Gimmnich P, Sanders K, Gekeler V. Metastasis of murine Renca kidney cancer cells to the lungs of Balb/c mice is strongly suppressed by TLR9 or TLR7 agonists. Abstract 3552, Proc Am Cancer Res 48, 2007), TOG=7-thia-8-oxoguanosine; IMDZQ=imidazoquinoline derivative). In particular, female Balb/c mice (n=10) were treated for 4 consecutive days starting day 1 or day 8 after Renca LacZ tumor cell injection, respectively. The compounds were applied in 20% PEG, ODNs in 0.9% NaCl as indicated. Lungs were excised 25 days after tumor cell injection.
Figure 4B:
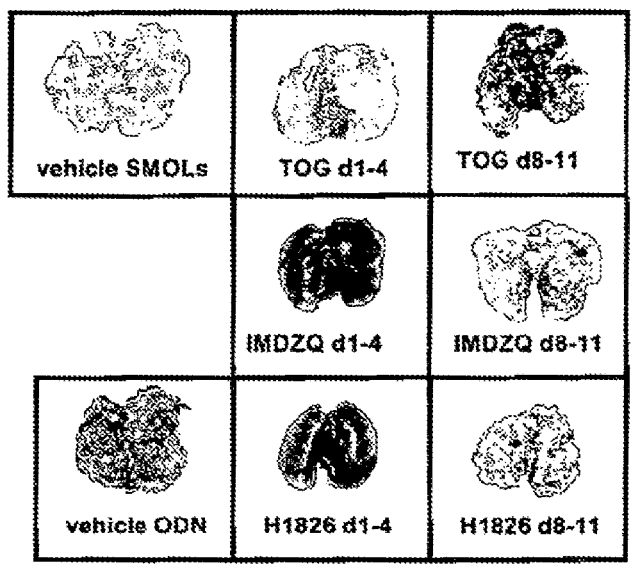
FIG. 4B shows studies with reference compounds in the Renca lung metastasis model (Leja A, Hofmann H P, Maier T, Drache D, Grebe C, Fischer S, Gimmnich P, Sanders K, Gekeler V. Metastasis of murine Renca kidney cancer cells to the lungs of Balb/c mice is strongly suppressed by TLR9 or TLR7 agonists. Abstract 3552, Proc Am Cancer Res 48, 2007), TOG=7-thia-8-oxoguanosine; IMDZQ=imidazoquinoline derivative). In particular, female Balb/c mice (n=10) were treated for 4 consecutive days starting day 1 or day 8 after Renca LacZ tumor cell injection, respectively. The compounds (small molecules (SMOLs)) were applied in 20% PEG, ODNs in 0.9% NaCl as indicated. Lungs were excised 25 days after tumor cell injection.
Figure 4C:
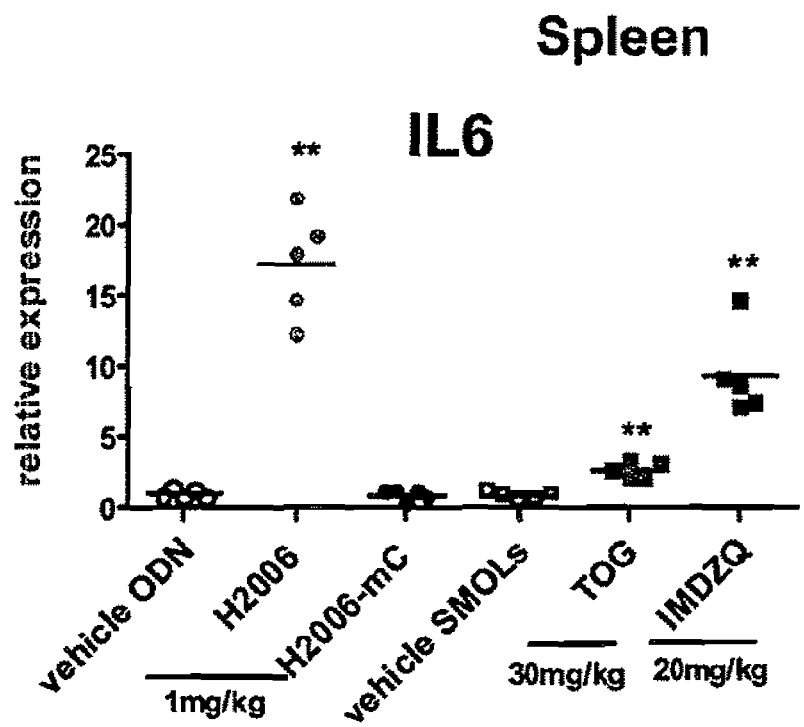
FIG. 4C shows female Balb/c mice (n=5) were treated for 4 consecutive days as indicated. The compounds were applied in 20% PEG, ODNs in 0.9% NaCl. At day 4 of treatment, blood was collected via orbital plexus and spleens were excised. Subsequently, mRNA was isolated for expression analysis via qPCR. Data were normalized to vehicle control (mean set to 1). Statistical evaluation was performed via Mann-Whitney test.
Figure 4D:
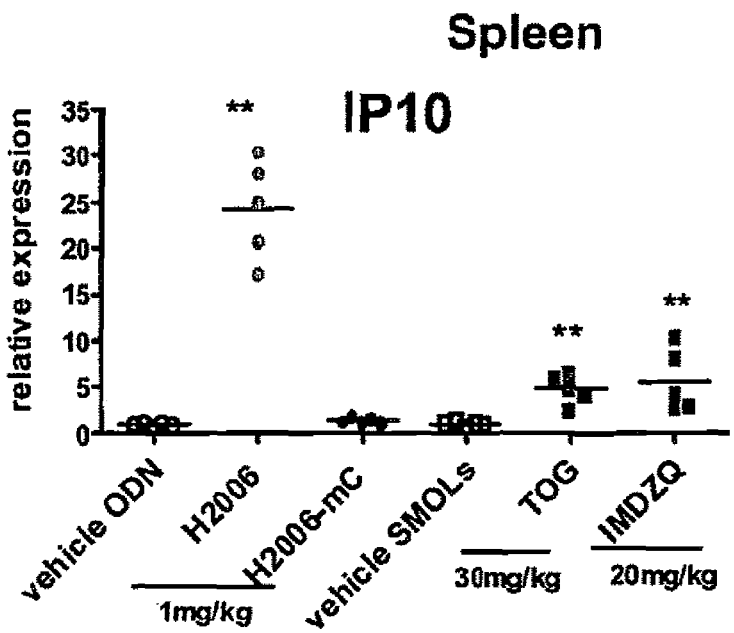
FIG. 4D shows female Balb/c mice (n=5) were treated for 4 consecutive days as indicated. The compounds (SMOLs) were applied in 20% PEG, ODNs in 0.9% NaCl. At day 4 of treatment, blood was collected via orbital plexus and spleens were excised. Subsequently, mRNA was isolated for expression analysis via qPCR. Data were normalized to vehicle control (mean set to 1). Statistical evaluation was performed via Mann-Whitney test.
Figure 4E:
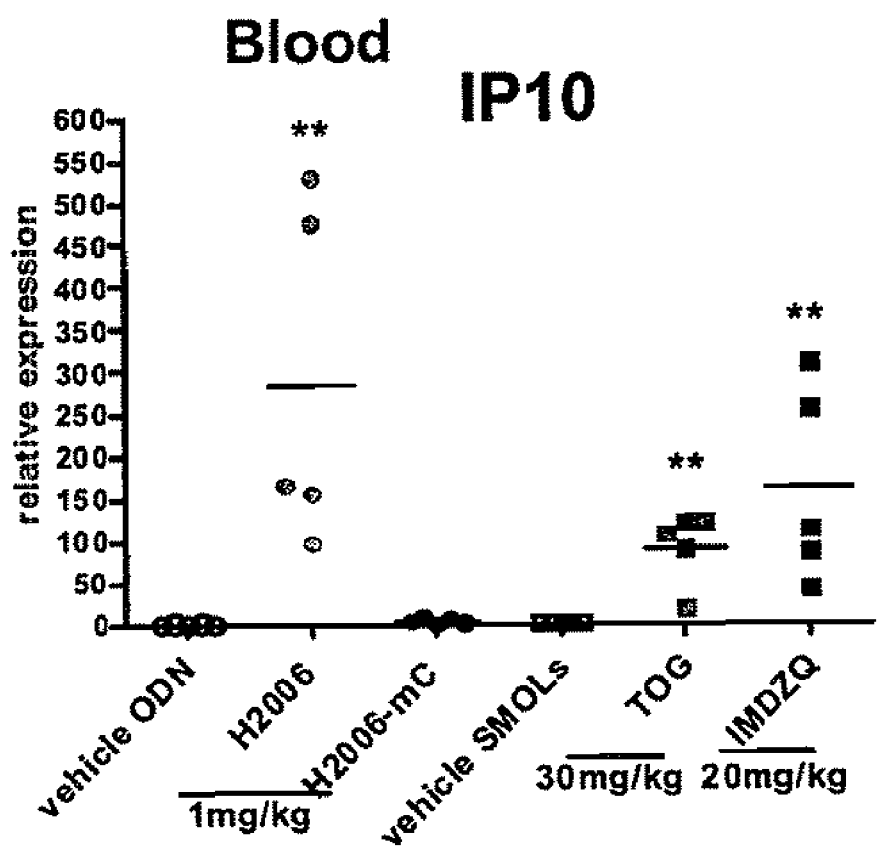
FIG. 4E shows female Balb/c mice (n=5) were treated for 4 consecutive days as indicated. The compounds (SMOLs) were applied in 20% PEG, ODNs in 0.9% NaCl. At day 4 of treatment, blood was collected via orbital plexus and spleens were excised. Subsequently, mRNA was isolated for expression analysis via qPCR. Data were normalized to vehicle control (mean set to 1). Statistical evaluation was performed via Mann-Whitney test.

FIGS. 4A and 4B show the results of reference compounds (TLR9 as well as TLR7 agonists, which are either SMOLs or oligonucleotides; TOG=7-thia-8-oxoguanosine; IMDZQ=imidazoquinoline derivative).

In particular, female Balb/c mice (n=10) were treated for 4 consecutive days starting day 1 or day 8 after Renca LacZ tumor cell injection, respectively. The SMOLs were applied in 20% PEG, the oligonucleotides in 0.9% NaCl as indicated. Lungs were excised 25 days after tumor cell injection (see FIG. 4A). Further, female Balb/c mice (n=5) were treated for 4 consecutive days as indicated. The SMOLs were applied in 20% PEG, oligonucleotides in 0.9% NaCl. At day 4 of treatment, blood was collected via orbital plexus and spleens were excised. Subsequently, mRNA was isolated for expression analysis via qPCR. Data were normalized to vehicle control (mean set to 1). Statistical evaluation was performed via Mann-Whitney test (see FIG. 4B).

Under the same conditions as described above for the SMOLs as reference compounds, 3-{acetyl[4-(4-amino-2-ethyl-1H-imidazo[4,5-c]quinolin-1-yl)butyl]amino}-2,5-anhydro-1,3,4-trideoxypentitol (TLR ago 1, example III) and N-[4-(4-amino-2-ethyl-1H-imidazo[4,5-c]quinolin-1-yl)butyl]-N-(1,1-dioxidotetrahydro-3-thienyl) acetamide (TLR ago 2, example I) TLR ago 1, both compounds according to the invention, are examined in the Renca lung metastasis model.

3-{acetyl[4-(4-amino-2-ethyl-1H-imidazo[4,5-c]quinolin-1-yl)butyl]amino}-2,5-anhydro-1,3,4-trideoxypentitol (TLR ago 1, example III) demonstrates a strong anti-metastatic effect with virtually complete clearance of the lungs after a short treatment (d1-4) (FIG. 5).

The invention claimed is:
1. A method for treating a disease sensitive to TLR7 activation, or a method for treating a cancer sensitive to the activation of TLR7, or a method for treating a viral or neoplastic disease, or a method for activating TLR7, comprising administering to a subject in need thereof an effective amount of a compound of formula I

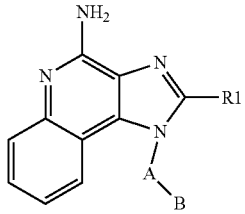

wherein
$R_1$ is selected from the group consisting of:
  alkyl, alkynyl, aryl, alkoxy, heterocyclyl and heteroaryl,
  which alkyl, alkynyl, aryl, alkoxy, heterocyclyl or heteroaryl is unsubstituted or substituted by one or more substituents;
A is $C_1$-$C_6$ alkyl;
B is —$N(R_2)(R_3)$;
$R_2$ is H or —(CO)—$R_5$;
$R_5$ is selected from the group consisting of:
  alkyl, cycloalkyl, alkynyl, and heterocyclyl,
    each of which is unsubstituted or substituted by one or more substituents;
$R_3$ is heterocyclyl,
  which heterocyclyl is unsubstituted or substituted by one or more substituents;
or a pharmaceutically acceptable solvate, salt, N-oxide or stereoisomer thereof,
wherein at least one of the following conditions i to iv is satisfied:
  i) $R_2$ is —(CO)—$R_5$;
  ii) A is not propyl;
  iii) $R_1$ is not butyl;
  iv) $R_3$ does not encompass substituted piperidyl.

2. A method according to claim 1, which is for treating a disease sensitive to TLR7 activation.

3. A method according to claim 1, which is for treating a cancer sensitive to the activation of TLR7.

4. A method according to claim 1, which is for treating a viral or neoplastic disease.

5. A method according to claim 1, which is for activating TLR7.

6. A method for treating a disease sensitive to TLR7 activation, or a method for treating a cancer sensitive to the activation of TLR7, or a method for treating a viral or neoplastic disease, or a method for activating TLR7,
  comprising administering to a subject in need thereof an effective amount of one of the following compounds
  N-[4-(4-amino-2-ethyl-1H-imidazo[4,5-c]quinolin-1-yl)butyl]-N-(1,1-dioxidotetrahydro-3-thienyl)acetamide,
  N-[4-(4-amino-2-ethyl-1H-imidazo[4,5-c]quinolin-1-yl)butyl]-N-(1-methyl-1-oxidopiperidin-4-yl)acetamide,
  3-{acetyl[4-(4-amino-2-ethyl-1H-imidazo[4,5-c]quinolin-1-yl)butyl]amino}-2,5-anhydro-1,3,4-trideoxypentitol,
  N-[4-(4-amino-2-ethyl-1H-imidazo[4,5-c]quinolin-1-yl)butyl]-N-(1-benzyl-2-methyl-1-oxidopyrrolidin-3-yl)acetamide,
  2-ethyl-1-[4-(tetrahydro-2H-pyran-4-ylamino)butyl]-1H-imidazo[4,5-c]quinolin-4-amine,
  1-[4-(1-azabicyclo[2.2.2]oct-3-ylamino)butyl]-2-ethyl-1H-imidazo[4,5-c]quinolin-4-amine or
  1-{4-[(1,1-dioxido-3,4-dihydro-2H-thiochromen-4-yl)amino]butyl}-2-ethyl-1H-imidazo[4,5-c]quinolin-4-amine,
or a pharmaceutically acceptable solvate, salt, N-oxide or stereoisomer thereof.

7. A method according to claim 1, wherein a compound of formula I or a pharmaceutically acceptable solvate, salt, N-oxide or stereoisomer thereof is administered, wherein, in the compound of formula I,
$R_1$ is selected from the group consisting of:
  alkyl, alkynyl, aryl, alkoxy, heterocyclyl and heteroaryl,
  which alkyl, alkynyl, aryl, alkoxy, heterocyclyl or heteroaryl is unsubstituted or substituted by one or more substituents selected from the group consisting of: —H, —OH, halogen, —CO—$N(R_4)_2$, —$N(R_4)_2$, —CO—$C_{1-10}$ alkyl, —CO—O—$C_{1-10}$ alkyl, —$N_3$, optionally substituted aryl, heterocyclyl and —CO-aryl,
    wherein each $R_4$ is independently —H, —$C_{1-10}$ alkyl, —$C_{1-10}$ alkyl-aryl, or aryl;
A is $C_1$-$C_6$ alkyl;
B is —$N(R_2)(R_3)$;
$R_2$ is H or —(CO)—$R_5$;
$R_5$ is selected from the group consisting of:
  alkyl, cycloalkyl, alkynyl, and heterocyclyl,
    each of which is unsubstituted or substituted by one or more substituents selected from the group consisting of: —H, —OH, halogen, —CN, —$NO_2$, —COOH, —SH, —CO—$C_{1-6}$ alkyl, —CO—O—$C_{1-6}$ alkyl, —$N_3$, optionally substituted aryl, heterocyclyl, —CO-aryl and —CO-heterocyclyl;
$R_3$ is
heterocyclyl,
  which heterocyclyl is unsubstituted or substituted by one or more substituents selected from group consisting of: —H, alkyl, alkenyl, alkoxy, halogen, —OH, —$N_3$, trifluromethyl, -alkyl-aryl, —O-alkyl-aryl, —CO-aryl, aryl, heterocyclyl, heteroaryl, CO-heteroaryl, —CO-substituted aryl, CO-substituted heteroaryl, —CO—O-alkyl, —CO—N-alkyl, and —CO—N-aryl;
wherein at least one of the following conditions i to iv is satisfied:
  i) $R_2$ is —(CO)—$R_5$;
  ii) A is not propyl;
  iii) $R_1$ is not butyl;
  iv) $R_3$ is not substituted piperidyl.

8. A method according to claim 6, wherein one of the following compounds is administered
  N-[4-(4-amino-2-ethyl-1H-imidazo[4,5-c]quinolin-1-yl)butyl]-N-(1,1-dioxidotetrahydro-3-thienyl)acetamide,
  N-[4-(4-amino-2-ethyl-1H-imidazo[4,5-c]quinolin-1-yl)butyl]-N-(1-methyl-1-oxidopiperidin-4-yl)acetamide,
  3-{acetyl[4-(4-amino-2-ethyl-1H-imidazo[4,5-c]quinolin-1-yl)butyl]amino}-2,5-anhydro-1,3,4-trideoxypentitol,
  N-[4-(4-amino-2-ethyl-1H-imidazo[4,5-c]quinolin-1-yl)butyl]-N-(1-benzyl-2-methyl-1-oxidopyrrolidin-3-yl)acetamide,
  2-ethyl-1-[4-(tetrahydro-2H-pyran-4-ylamino)butyl]-1H-imidazo[4,5-c]quinolin-4-amine,
  1-[4-(1-azabicyclo[2.2.2]oct-3-ylamino)butyl]-2-ethyl-1H-imidazo[4,5-c]quinolin-4-amine or 1-{4-[(1,1-dioxido-3,4-dihydro-2H-thiochromen-4-yl) amino]butyl}-2-ethyl-1H-imidazo[4,5-c]quinolin-4-amine,
or a pharmaceutically acceptable salt thereof.

9. A method according to claim 1, wherein a compound of formula I or a pharmaceutically acceptable salt thereof is administered.

10. A method according to claim 1, wherein a compound of formula I or a pharmaceutically acceptable salt thereof is administered, wherein, in the compound of formula I,
$R_1$ is selected from the group consisting of:
alkyl, alkynyl, aryl, alkoxy, heterocyclyl and heteroaryl,
which alkyl, alkynyl, aryl, alkoxy, heterocyclyl or heteroaryl is unsubstituted or substituted by one or more substituents selected from the group consisting of: —H, —OH, halogen, —CO—N(R_4)_2, —N(R_4)_2, —CO—$C_{1-10}$ alkyl, —CO—O—$C_{1-10}$ alkyl, —N_3, optionally substituted aryl, heterocyclyl and —CO-aryl,
wherein each $R_4$ is independently —H, —$C_{1-10}$ alkyl, —$C_1$-10 alkyl-aryl, or aryl;
A is $C_1$-$C_6$ alkyl;
B is —N(R_2)(R_3);
$R_2$ is H or —(CO)—$R_5$;
$R_5$ is selected from the group consisting of:
alkyl, cycloalkyl, alkynyl, and heterocyclyl,
each of which is unsubstituted or substituted by one or more substituents selected from the group consisting of: —H, —OH, halogen, —CN, —NO_2, —COOH, —SH, —CO—$C_{1-6}$ alkyl, —CO—O—$C_{1-6}$ alkyl, —N_3, optionally substituted aryl, heterocyclyl, —CO-aryl and —CO-heterocyclyl;
$R_3$ is
heterocyclyl,
which heterocyclyl is unsubstituted or substituted by one or more substituents selected from group consisting of: —H, alkyl, alkenyl, alkoxy, halogen, —OH, —N_3, trifluromethyl, -alkyl-aryl, —O-alkyl-aryl, —CO-aryl, aryl, heterocyclyl, heteroaryl, CO-heteroaryl, —CO-substituted aryl, CO-substituted heteroaryl, —CO—O-alkyl, —CO—N-alkyl, and —CO—N-aryl;
wherein at least one of the following conditions i to iv is satisfied:
i) $R_2$ is —(CO)—$R_5$;
ii) A is not propyl;
iii) $R_1$ is not butyl;
iv) $R_3$ is not substituted piperidyl.

11. A method according to claim 1, wherein a compound of formula I or a pharmaceutically acceptable solvate, salt, N-oxide or stereoisomer thereof is administered, wherein, in the compound of formula I,
$R_3$ is heterocyclyl, which is unsubstituted or substituted by one or more substituents which are selected from group consisting of: —H, alkyl, alkenyl, halogen and —OH.

12. A method according to claim 1, wherein a compound of formula I or a pharmaceutically acceptable solvate, salt, N-oxide or stereoisomer thereof is administered, wherein, in the compound of formula I,
$R_3$ is selected from the group consisting of: dioxo-tetrahydrothiophenyl, tetrahydrofuranyl, tetrahydropyranyl and azabicyclooctanyl, each of which is optionally substituted by one or more substituents which are selected from group consisting of: —H, alkyl, alkenyl, halogen and —OH.

13. A method according to claim 1, wherein a compound of formula I or a pharmaceutically acceptable solvate, salt, N-oxide or stereoisomer thereof is administered, wherein, in the compound of formula I,
$R_1$ is alkyl and $R_5$ is alkyl.

14. A method according to claim 1, wherein a compound of formula I or a pharmaceutically acceptable solvate, salt, N-oxide or stereoisomer thereof is administered, wherein, in the compound of formula I,
$R_2$ is H.

15. A method according to claim 1, wherein a compound of formula I or a pharmaceutically acceptable solvate, salt, N-oxide or stereoisomer thereof is administered, wherein, in the compound of formula I, only condition i) is satisfied.

16. A method according to claim 1, wherein a compound of formula I or a pharmaceutically acceptable solvate, salt, N-oxide or stereoisomer thereof is administered, wherein, in the compound of formula I, only condition ii) is satisfied.

17. A method according to claim 1, wherein a compound of formula I or a pharmaceutically acceptable solvate, salt, N-oxide or stereoisomer thereof is administered, wherein, in the compound of formula I, only condition iii) is satisfied.

18. A method according to claim 1, wherein a compound of formula I or a pharmaceutically acceptable solvate, salt, N-oxide or stereoisomer thereof is administered, wherein, in the compound of formula I, only condition iv) is satisfied.

19. A method for treating a disease sensitive to TLR7 activation, or a method for treating a cancer sensitive to the activation of TLR7, or a method for treating a viral or neoplastic disease, or a method for activating TLR7,
comprising administering to a subject in need thereof an effective amount a compound of formula I

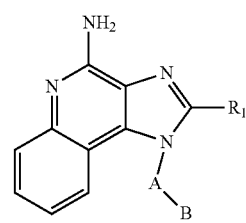

(I)

wherein
$R_1$ is selected from the group consisting of:
H, alkyl, alkynyl, aryl, alkoxy, heterocyclyl and heteroaryl,
which alkyl, alkynyl, aryl, alkoxy, heterocyclyl or heteroaryl is unsubstituted or substituted by one or more substituents;
A is $C_1$-$C_6$ alkyl;
B is —N(R_2)(R_3);
$R_2$ is H or —(CO)—$R_5$;
$R_5$ is selected from the group consisting of:
alkyl, cycloalkyl, alkynyl, aryl, heterocyclyl and heteroaryl,
each of which is unsubstituted or substituted by one or more substituents;
$R_3$ is selected from the group consisting of:
—H, alkyl, alkenyl, aryl, heteroaryl, cycloalkyl, and heterocyclyl,
which alkyl, alkenyl, aryl, heteroaryls, cycloalkyl or heterocyclyl is unsubstituted or substituted by one or more substituents;

or a pharmaceutically acceptable solvate, salt, N-oxide or stereoisomer thereof.

20. A method according to claim 1, wherein a compound of formula I or a pharmaceutically acceptable solvate, salt, N-oxide or stereoisomer thereof is administered, wherein, in the compound of formula I, $R_2$ is —(CO)—$R_5$.

* * * * *